(12) United States Patent
Li et al.

(10) Patent No.: US 10,947,182 B1
(45) Date of Patent: Mar. 16, 2021

(54) CINNAMYL ALCOHOL CASSIC ACID ESTER WITH ANTIBACTERIAL ACTIVITY AND A METHOD OF PREPARING THE SAME

(71) Applicants: Han Li, Xi'an (CN); Nan Hui, Xi'an (CN); Chengyuan Liang, Xi'an (CN); Xingke Ju, Xi'an (CN); Guaiping Qiao, Xi'an (CN); Juan Li, Xi'an (CN); Yuanyuan He, Xi'an (CN); Bin Tian, Xi'an (CN); Yongbo Wang, Xi'an (CN); Jingwen Xu, Xi'an (CN); Liang Qi, Xi'an (CN); Dan Yang, Xi'an (CN); Qiangian Zhao, Xi'an (CN); Yanjun Li, Xi'an (CN); Qiao Zeng, Xi'an (CN); Gennian Mao, Xi'an (CN); Limei Wang, Xi'an (CN)

(72) Inventors: Han Li, Xi'an (CN); Nan Hui, Xi'an (CN); Chengyuan Liang, Xi'an (CN); Xingke Ju, Xi'an (CN); Guaiping Qiao, Xi'an (CN); Juan Li, Xi'an (CN); Yuanyuan He, Xi'an (CN); Bin Tian, Xi'an (CN); Yongbo Wang, Xi'an (CN); Jingwen Xu, Xi'an (CN); Liang Qi, Xi'an (CN); Dan Yang, Xi'an (CN); Qiangian Zhao, Xi'an (CN); Yanjun Li, Xi'an (CN); Qiao Zeng, Xi'an (CN); Gennian Mao, Xi'an (CN); Limei Wang, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 16/914,326

(22) Filed: Jun. 27, 2020

(51) Int. Cl.
*C07C 69/94* (2006.01)

(52) U.S. Cl.
CPC ..................... *C07C 69/94* (2013.01)

(58) Field of Classification Search
CPC ....................................... C07C 69/94
See application file for complete search history.

(56) References Cited

U.S. PATENT DOCUMENTS

2015/0203442 A1* 7/2015 Wang ................. A61P 43/00
514/626

* cited by examiner

*Primary Examiner* — Yevgeny Valenrod
*Assistant Examiner* — Blaine G Doletski

(57) ABSTRACT

A compound having the formula (I):

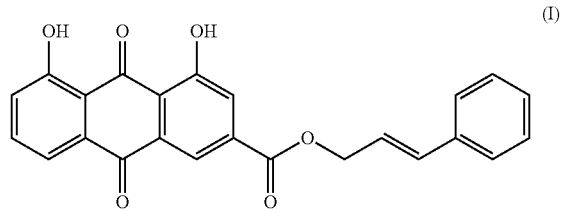

is disclosed. A method of preparing the compound of formula (I) is also disclosed.

15 Claims, 3 Drawing Sheets

CINNAMYL ALCOHOL CASSIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a cinnamyl alcohol cassic acid ester with anti-resistant bacteria activity and a method of preparing the same.

BACKGROUND OF THE INVENTION

The emergence of antibiotics has effectively controlled many bacterial infectious diseases. However, with the use of antibiotics, bacterial resistance has become an extremely serious worldwide problem and has become one of the medical hot spots in this century. In recent years, there have been more and more drug-resistant bacteria, and the scope of drug resistance has become wider and wider, making it difficult to treat these bacteria. It is imminent to find and develop new anti-resistant bacteria drugs.

Cassic acid (also known as rhein) is a natural anthraquinone compound (compound of formula II), which has a variety of biological and pharmacological activities and can be extracted from rhubarb. It has many effects, such as improving glucose and lipid metabolism, protecting liver, anti-fibrosis, anti-oxidation, anti-inflammation, antibacterial, anti-cancer and anti-tumor. However, its clinical application is limited to a great extent because of its poor water solubility and low bioavailability.

Cinnamyl alcohol is an organic compound that is found in cinnamon leaves. It can be used to prepare strawberry, lemon, apricot, peach and other fruit flavors and brandy flavors.

In the present invention, cassic acid is modified by the cinnamyl alcohol structure to obtain a cinnamyl alcohol cassic acid ester. Preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a compound having formula (I) (cinnamyl alcohol cassic acid ester).

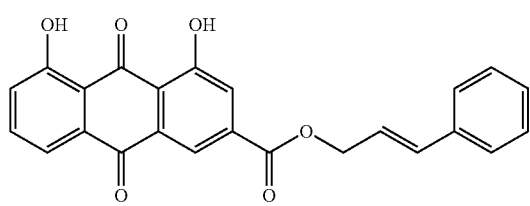

(I)

In another embodiment, the present invention provides a method of preparing the compound of formula (I). The method includes: reacting the compound of formula (II) with the compound of formula (III) to obtain the compound of formula (I):

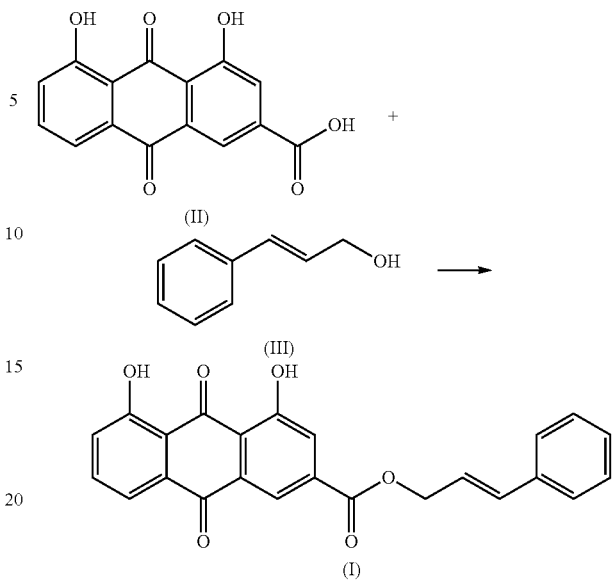

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 50-80° C. for 4-8 hours; concentrating the reaction mixture and extracting the reaction mixture with ethyl acetate to obtain a crude product; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is toluene.

In another embodiment, the molar ratio of the compound of formula (II) and the compound of formula (III) is 1:1.1.

In another embodiment, the reaction mixture is heated at 70° C.

In another embodiment, the reaction mixture is heated for 6 hours.

In another embodiment, the eluent is petroleum ether: ethyl acetate=1:3.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][$BF_4$]).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 25° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
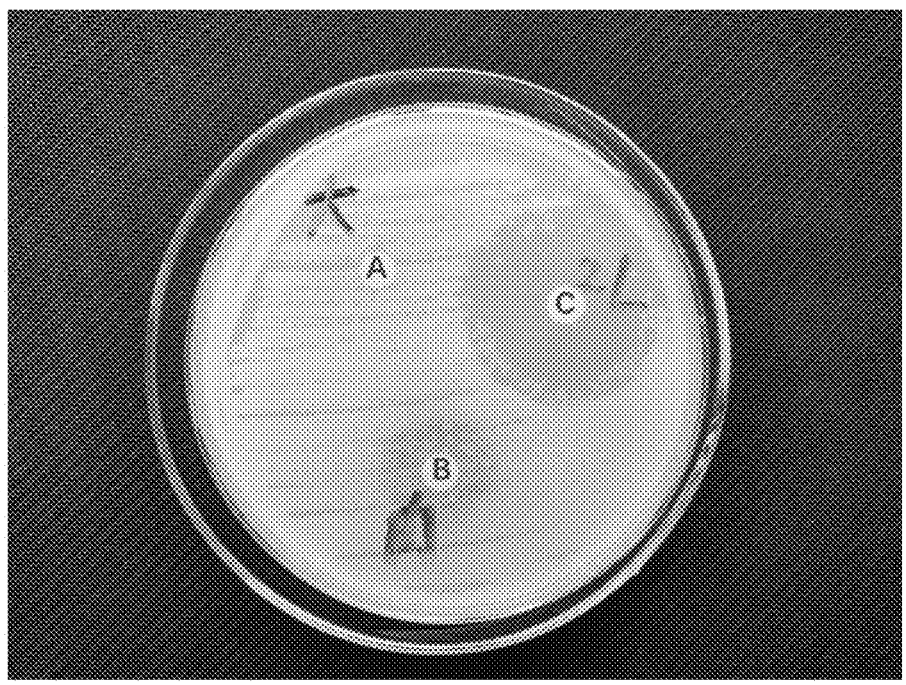
FIG. 1 shows the antibacterial effect of cassic acid, cinnamyl alcohol and cefazolin on *Staphylococcus aureus*.

Reference will now be made in detail to embodiments of the present invention, example of which is illustrated in the accompanying drawings. The following examples illustrate the present invention, but the present invention is not limited to the following examples.

Example 1

Preparation of Compound Cinnamyl 4,5-dihydroxy-9,10-dioxo-9,10-dihydroanthracene-2-carboxylate (Cinnamyl Alcohol Cassic Acid Ester, Compound of Formula I)

In a 250 mL three-necked flask, 198.8 mg (0.70 mmol) of cassic acid and 134.2 mg (0.70 mmol) EDC (1-ethyl-3-(3-dimethylaminopropyl)carbodiimide) were dissolved in 100 mL of toluene under nitrogen atmosphere. 103.2 mg (0.77 mmol) of cinnamyl alcohol was dissolved in 20 mL of toluene, and slowly added dropwise to the reaction liquid by a separatory funnel. After the completion of the dropwise addition, the temperature was raised to 70° C., and the reaction was carried out for 6 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 206.8 mg of the title compound, a yield of 73.83%.

$^1$H-NMR (400 MHz, DMSO-d$^6$) δ (ppm): 8.17 (1H, d), 7.88 (1H, d), 7.84 (1H, s), 7.78 (1H, s), 7.45 (2H, d), 7.37 (3H, d), 7.26 (1H, d), 6.60 (1H, d), 6.56 (1H, d), 6.43 (2H, s), 4.85 (2H, d); $^{13}$C-NMR (400 MHz, DMSO-d$^6$) δ (ppm): 191.8, 181.4, 165.9, 161.9, 161.6, 137.4, 134.3, 133.7, 131.3, 129.0, 127.6, 126.6, 125.1, 124.6, 119.9, 119.3, 116.6, 61.9.

Example 2

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid and 134.2 mg (0.70 mmol) EDC were dissolved in 100 mL of acetonitrile under nitrogen atmosphere. 103.2 mg (0.77 mmol) of cinnamyl alcohol was dissolved in 20 mL of acetonitrile, and slowly added dropwise to the reaction liquid by a separatory funnel. After the completion of the dropwise addition, the temperature was raised to 80° C., and the reaction was carried out for 4 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 176.7 mg of the title compound, a yield of 63.11%.

Example 3

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid and 134.2 mg (0.70 mmol) EDC were dissolved in 100 mL of tetrahydrofuran under nitrogen atmosphere. 103.2 mg (0.77 mmol) of cinnamyl alcohol was dissolved in 20 mL of tetrahydrofuran, and slowly added dropwise to the reaction liquid by a separatory funnel. After the completion of the dropwise addition, the temperature was raised to 70° C., and the reaction was carried out for 7 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 195.6 mg of the title compound, a yield of 69.85%.

Example 4

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid and 134.2 mg (0.70 mmol) EDC were dissolved in 100 mL of acetonitrile under nitrogen atmosphere. 112.6 mg (0.84 mmol) of cinnamyl alcohol was dissolved in 20 mL of acetonitrile, and slowly added dropwise to the reaction liquid by a separatory funnel. After the completion of the dropwise addition, the temperature was raised to 60° C., and the reaction was carried out for 7 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 180.0 mg of the title compound, a yield of 64.28%.

Example 5

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid and 134.2 mg (0.70 mmol) EDC were dissolved in 100 mL of toluene under nitrogen atmosphere. 103.2 mg (0.77 mmol) of cinnamyl alcohol was dissolved in 20 mL of toluene, and slowly added dropwise to the reaction liquid by a separatory funnel. After the completion of the dropwise addition, the temperature was raised to 80° C., and the reaction was carried out for 5 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 182.6 mg of the title compound, a yield of 65.21%.

Example 6

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid and 134.2 mg (0.70 mmol) EDC were dissolved in 100 mL of tetrahydrofuran under nitrogen atmosphere. 103.2 mg (0.77 mmol) of cinnamyl alcohol was dissolved in 20 mL of tetrahydrofuran, and slowly added dropwise to the reaction liquid by a separatory funnel. After the completion of the dropwise addition, the temperature was raised to 65° C., and the reaction was carried out for 6 hours. Thin layer chromatography was used to track the reaction to completion, heating was stopped, and the protective device was removed. The concentrated solution was washed in water, extracted with chloroform, dried and concentrated, and a crude product was obtained. The crude product was further purified by silica gel column chromatography, petroleum ether:ethyl acetate=1:3 as eluent, and the eluent was concentrated under reduced pressure and dried to obtain 169.0 mg of the title compound, a yield of 60.35%.

Example 7

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid, 103.2 mg (0.77 mmol) of cinnamyl alcohol and 12.0 mg (0.007 mmol) silicomolybdic acid were dissolved in 80 mL of 1-butyl-3-methylimidazolium tetrafluoroborate under nitrogen atmosphere. After full dissolution, the temperature was raised to 25° C. and the reaction was carried out for 8 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain 240.4 mg of the title compound, a yield of 85.84%.

Example 8

Preparation of Compound Cinnamyl 4,5-dihydroxy-9,10-dioxo-9,10-dihydroanthracene-2-carboxylate In a 250 mL three-necked flask, 198.8 mg (0.70 mmol) of cassic acid, 103.2 mg (0.77 mmol) of cinnamyl alcohol and 12.0 mg (0.007 mmol) silicomolybdic acid were dissolved in 80 mL of 1-butyl-3-methylimidazolium tetrafluoroborate under nitrogen atmosphere. After full dissolution, the temperature was raised to 50° C. and the reaction was carried out for 5 hours. Thin layer chromatography was used to track the reaction to completion, heating was stopped, and the protective device was removed. The reaction mixture system was allowed to separate into layers to give a crude product. The crude product was recrystallized with 50 mL methanol and dried to obtain 228.2 mg of the title compound, a yield of 81.47%.

Example 9

Antibacterial Activity Test of the Compounds of the Invention

The antimicrobial efficacy was determined by a paper diffusion method drug sensitivity test.

Experimental strains: *Staphylococcus aureus* (SAU), multi-resistant *Staphylococcus aureus* 18-206. The experimental strain was identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was cefazolin (30 μg/tablet); the test drugs were cassic acid (30 μg/tablet), cinnamyl alcohol (30 μg/tablet) and cinnamyl alcohol cassic acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 10^8$ CFU/mL). A bacterial suspension is obtained.

Paper Diffusion Method Drug Sensitivity Test:

Weigh the LB dry powder, sterilize at 103.4 Kpa, 121.3° C. high-pressure steam for 15 min, and then put it in a 40° C.-50° C. water bath. Place a sterile empty plate (inner diameter 9 cm) on the surface of the ultra-clean table water table, shake and shake LB, and then pour the plate. The thickness of each plate is 3 mm to 4 mm. After the plate is cooled at room temperature, store it in the refrigerator at 2° C.-8° C. Use a sterile cotton swab to dip the bacterial solution, and evenly coat the surface of the LB plate 3 times. After inoculation of the bacterial suspension, the LB plate was dried at room temperature for 3 min to 5 min. Use sterile forceps to closely attach the antibacterial drug paper to the dish. Put the dish upside down and place it in a 37° C. incubator for 24 h. Observe the result and measure the diameter. Taking 0.5% DMSO solution as a negative control, the antibacterial activity is expressed by the diameter of the inhibition zone. The inhibition zone ≥17 mm, sensitive; the inhibition zone is 15 mm-16 mm, intermediary; the inhibition zone ≤14 mm, drug resistance.

Figure 2:
FIG. 2 shows the antibacterial effect of cinnamyl alcohol cassic acid ester on *Staphylococcus aureus*.
Figure 3:
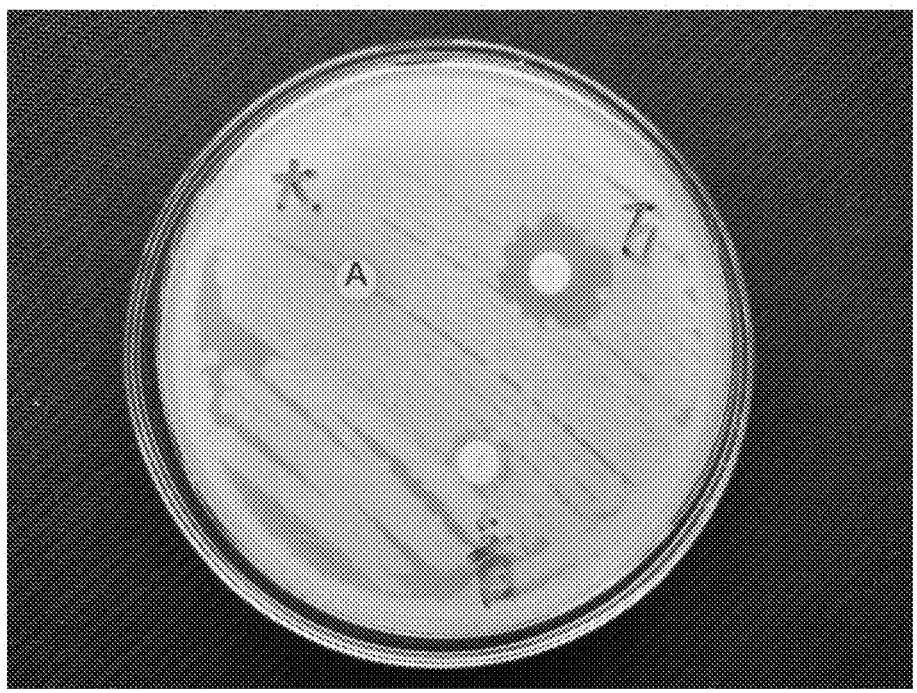
FIG. 3 shows the antibacterial effect of cassic acid on multi-resistant *Staphylococcus aureus* 18-206.
Figure 4:
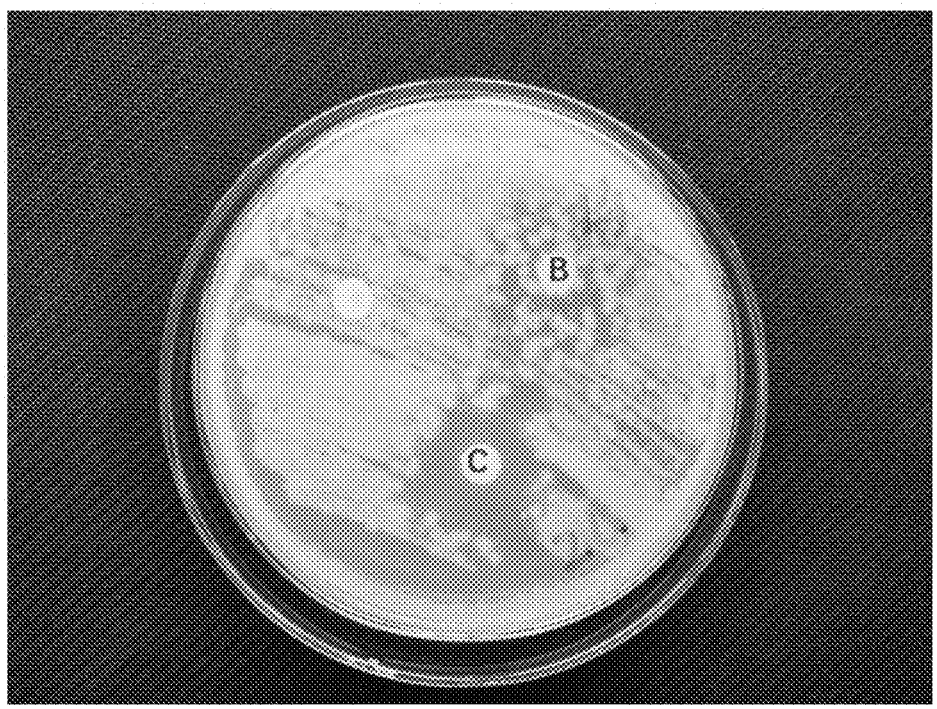
FIG. 4 shows the antibacterial effect of cinnamyl alcohol and cefazolin on multi-resistant *Staphylococcus aureus* 18-206.
Figure 5:
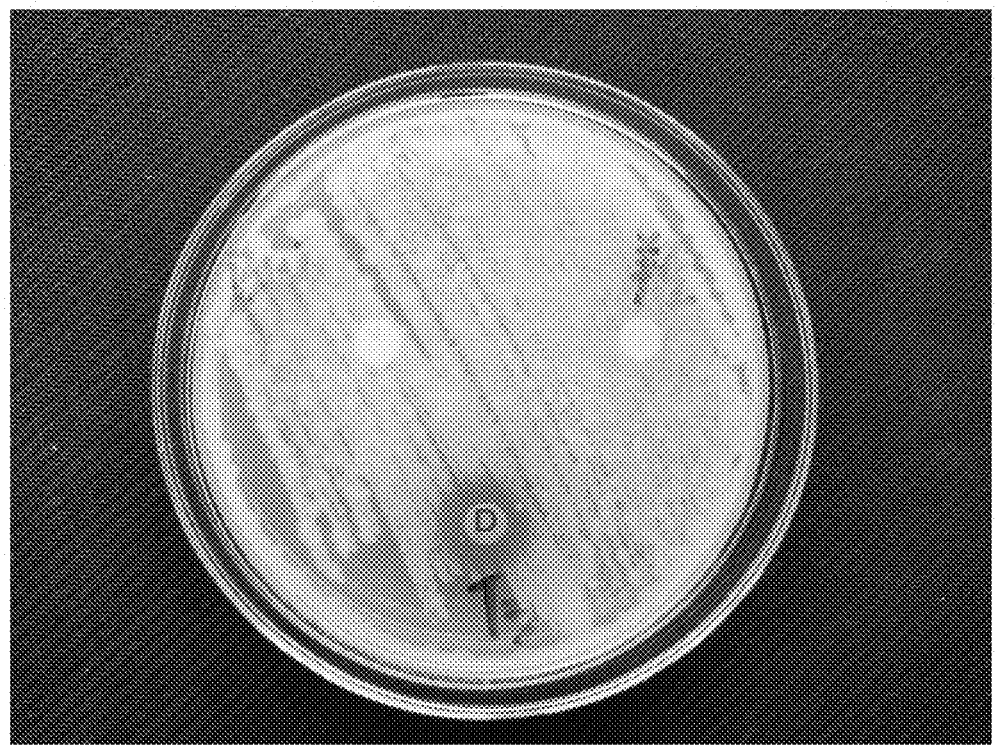
FIG. 5 shows the antibacterial effect of cinnamyl alcohol cassic acid ester on multi-resistant *Staphylococcus aureus* 18-206.

In FIGS. 1-5, cassic acid is represented by A; cinnamyl alcohol is represented by B, cefazolin is represented by C, and cinnamyl alcohol cassic acid ester is represented by D. FIG. 1 shows the antibacterial effect of cassic acid, cinnamyl alcohol and cefazolin on *Staphylococcus aureus*. FIG. 2 shows the antibacterial effect of cinnamyl alcohol cassic acid ester on *Staphylococcus aureus*. FIG. 3 shows the antibacterial effect of cassic acid on multi-resistant *Staphylococcus aureus* 18-206. FIG. 4 shows the antibacterial effect of cinnamyl alcohol and cefazolin on multi-resistant *Staphylococcus aureus* 18-206. FIG. 5 shows the antibacterial effect of cinnamyl alcohol cassic acid ester on multi-resistant *Staphylococcus aureus* 18-206. The results are shown in Table 1.

TABLE 1

Experimental Results of the Zone of Inhibition

| Compounds | Zone of inhibition /mm Strain | |
|---|---|---|
| | *Staphylococcus aureus* (SAU) | Multi-resistant *Staphylococcus aureus* 18-206 |
| 0.5% DMSO | 0 | 0 |
| Cefazolin | 34 | 22 |
| Cassic acid | 7 | 7 |
| Cinnamyl alcohol | 17 | 0 |
| Cinnamyl alcohol cassic acid ester | 13 | 15 |

The results show that cinnamyl alcohol has no inhibitory effect on drug-resistant bacteria, cassic acid has a weak inhibitory effect on drug-resistant bacteria, and cinnamyl alcohol cassic acid ester has strong suppression effect on multi-resistant *Staphylococcus aureus* 18-206. In summary, cinnamyl alcohol cassic acid ester of the present invention can be used as an antibacterial drug candidate for multi-resistant *Staphylococcus aureus*.

What is claimed is:

1. A compound of formula (I):

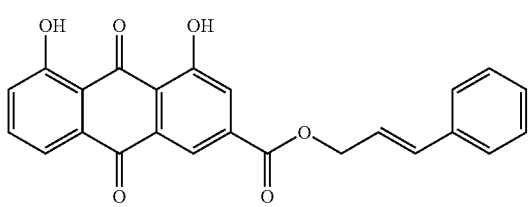

(I)

2. A method of preparing the compound of formula (I) of claim 1, comprising: reacting a compound of formula (II) with a compound of formula (III) to obtain the compound of formula (I):

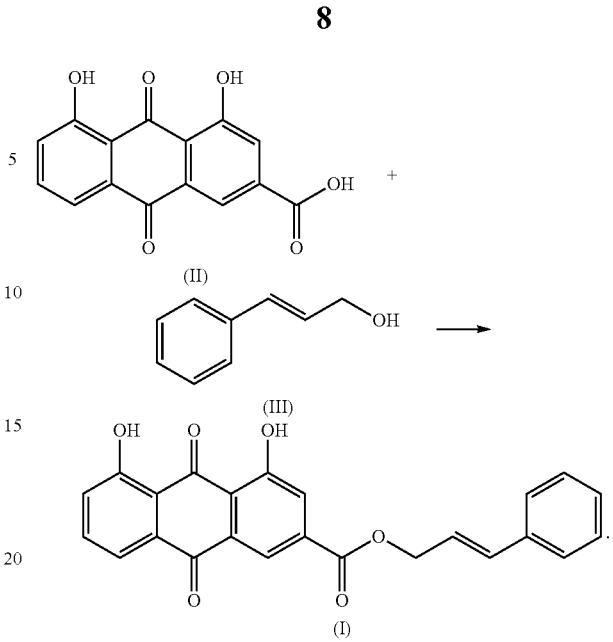

3. The method of claim 2, wherein the reaction of the compound of formula (II) with the compound of formula (III) comprises the following steps:
   placing the compound of formula (II) and the compound of formula (III), in a molar ratio of 1:1 to 1:1.3, in a reactor;
   adding an organic solvent and a catalytic amount of (1-ethyl-(3-dimethylaminopropyl)carbodiimide) under nitrogen atmosphere to obtain a reaction mixture; and
   heating the reaction mixture at 50-80° C. for 4-8 hours;
   concentrating the reaction mixture and extracting the reaction mixture with ethyl acetate to obtain a crude product; and
   purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 4, wherein the organic solvent is toluene.

6. The method of claim 3, wherein the molar ratio of the compound of formula (II) and the compound of formula (III) is 1:1.1.

7. The method of claim 3, wherein the reaction mixture is heated at 70° C.

8. The method of claim 3, wherein the reaction mixture is heated for 6 hours.

9. The method of claim 3, wherein the eluent is petroleum ether:ethyl acetate=1:3.

10. The method of claim 2, wherein the reaction of the compound of formula (II) with the compound of formula (III) comprises the following steps:
    placing the compound of formula (II), a catalyst, and an ionic liquid in a reactor under nitrogen atmosphere, the catalyst being 12-molybdosilicic acid hydrate ($H_6Mo_{12}O_{41}Si$);
    adding the compound of formula (III) to the reactor to form a reaction mixture;
    heating the reaction mixture at 20-50° C. for 5-10 hours;
    placing the reaction mixture in a separating funnel to separate a crude product;

purifying the crude product by recrystallization in methanol to obtain the compound of formula (I); and recycling the ionic liquid.

11. The method of claim 10, wherein the ionic liquid is 1-butyl-3-methylimidazolium tetrafluoroborate ([BMIM] [$BF_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 25° C.

15. The method of claim 10, wherein the reaction mixture is heated for 8 hours.

\* \* \* \* \*